(12) United States Patent
Choi et al.

(10) Patent No.: US 11,344,251 B2
(45) Date of Patent: May 31, 2022

(54) METHODS AND APPARATUS FOR THE ASSESSMENT OF GINGIVAL BLOOD FLOW (71) Applicant: The Regents of the University of California, Oakland, CA (US)

(72) Inventors: Bernard H. Choi, Irvine, CA (US); Petra Wilder-Smith, Irvine, CA (US); Bruce Y. Yang, Irvine, CA (US); Caitlin Regan, Irvine, CA (US); Sean M. White, Irvine, CA (US); Tyler Rice, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 304 days.

(21) Appl. No.: 15/612,889

(22) Filed: Jun. 2, 2017

(65) Prior Publication Data

US 2017/0347943 A1  Dec. 7, 2017

Related U.S. Application Data (60) Provisional application No. 62/345,653, filed on Jun. 3, 2016.

(51) Int. Cl.
*A61B 5/00* (2006.01)
*A61B 5/026* (2006.01)

(52) U.S. Cl.
CPC .......... *A61B 5/4552* (2013.01); *A61B 5/0088* (2013.01); *A61B 5/0261* (2013.01); *A61B 5/4848* (2013.01); *A61B 5/682* (2013.01); *A61B 5/7246* (2013.01); *Y02A 90/10* (2018.01)

(58) Field of Classification Search
None
See application file for complete search history.

(56) References Cited

U.S. PATENT DOCUMENTS

| | | | | |
|---|---|---|---|---|
| 5,016,098 A | * | 5/1991 | Cooper | A61B 1/00091 348/66 |
| 6,201,880 B1 | * | 3/2001 | Elbaum | A61B 1/24 348/66 |
| 2008/0026340 A1 | * | 1/2008 | Gerlach | A61B 5/0088 433/29 |
| 2008/0287808 A1 | * | 11/2008 | Tearney | A61B 5/445 600/476 |
| 2012/0301839 A1 | * | 11/2012 | Stoianovici | A61B 5/0088 433/27 |

* cited by examiner

*Primary Examiner* — Jonathan Cwern
(74) *Attorney, Agent, or Firm* — Master Key IP, LLP; Justin G. Sanders (57) ABSTRACT

Disclosed herein are methods and apparatus for diagnosing a disease in the gingival region of an individual, comprising: quantitatively measuring blood flow or changes in blood flow in the gingival region of the individual, potentially comparing these data to that of a healthy subject, and diagnosing the disease based one of more of these quantities.

16 Claims, 8 Drawing Sheets

METHODS AND APPARATUS FOR THE ASSESSMENT OF GINGIVAL BLOOD FLOW

CROSS REFERENCE TO RELATED APPLICATIONS

The present application claims priority to U.S. Provisional Patent Application Ser. No. 62/345,653 filed Jun. 3, 2016, the contents which are incorporated herein by reference.

STATEMENT REGARDING FEDERALLY SPONSORED RESEARCH OR DEVELOPMENT

This invention was made with Government support under Grant No. DE022831 awarded by the National Institutes of Health. The Government has certain rights in this invention.

FIELD OF THE INVENTION

The present disclosure is in the field of photonics, dentistry, and medicine, specifically laser speckle imaging.

BACKGROUND OF THE DISCLOSURE

Gingivitis is a disease caused by a buildup of plaque, a bacterial biofilm, on the teeth and in the gingival sulcus. Symptoms of gingivitis include inflammation of the gingiva, which can result in redness, tenderness, and swelling of the gums, as well as bleeding during brushing or flossing. Current methods to diagnose gingivitis include visual inspection and mechanical probing of the gingiva by a dentist who scores gingival health on a 0-3 scale. However, the results of this assessment technique have been shown to be qualitative and subjective. Alternatively, enzymatic biomarkers in the saliva can be used for diagnosis, but such tests are time consuming and expensive.

Currently available methods in this field to assess blood flow and inflammation revolve around a technology known as laser Doppler flowmetry. However there are several disadvantages of laser Doppler flowmetry, such as pressure artifact, limited penetration depth and small region of interrogation.

Thus there exists a need in the art for an improved method and apparatus for evaluating the gingival region.

SUMMARY OF THE DISCLOSURE

Various embodiments disclosed herein include a method of assessing and/or diagnosing a disease in the gingival region of an individual, comprising: quantitatively measuring blood flow at one or more time points in the gingival region of the individual; and assessing and/or diagnosing the disease by comparing the blood flow at the one or more time points. In one embodiment, the disease is gingivitis. In one embodiment, the blood flow is measured by transmission laser speckle imaging (LSI) through the gingival region. In one embodiment, the blood flow is measured by a change in speckle pattern over time. In one embodiment, the blood flow is measured by one or more of the following steps: illuminating the gingival, capturing one or more laser speckle images produced by scattering of light off the gingiva, determining change in speckle pattern over time, and evaluating blood flow changes based on change in speckle patterns over time. In one embodiment, the blood flow is measured by an apparatus comprising a light source and a detector for detecting transmission of light through the gingiva region of the individual. In one embodiment, the blood flow is measured in real time. In one embodiment, the method further comprises treating the individual diagnosed with the disease by administering an effective amount of a medical composition for treating the disease. In one embodiment, the method further comprises one or more optics for directing the light source onto the gingiva region of the individual. In one embodiment, the method further comprises measuring a change in blood flow at one or more time points in the gingival region of the individual relative to a healthy subject. In one embodiment, the change in blood flow is associated with gingival inflammation.

Various embodiments disclosed herein also include an apparatus, comprising: a light source; and a detector for detecting transmission of light through the gingiva region of a subject. In one embodiment, the detector quantitatively measures gingival perfusion and/or blood flow at one or more time points. In one embodiment, the light source comprises a laser diode. In one embodiment, the detector comprises a camera. In one embodiment, the apparatus is adapted to fit partially or wholly within the mouth of the subject. In one embodiment, the apparatus is adapted to fit in place partially or wholly within the mouth of the subject by custom molds. In one embodiment, the custom molds are from dental putty.

Other embodiments disclosed herein include a method of determining an efficacy of a gingivitis treatment in a patient, comprising: measuring blood flow through the gingival region of a patient at the start of a treatment; measuring blood flow through the gingival region of the patient at the end of a treatment; and determining efficacy of the treatment based on the change in blood flow at the end of the treatment relative to the start of the treatment. In one embodiment, the blood flow is measured by one or more of the following steps: illuminating the gingival, capturing one or more laser speckle images produced by scattering of light off the gingiva, and evaluating blood flow based on contrast of the speckle pattern at one more time points. In one embodiment, the change in blood flow is measured by transmission laser speckle imaging (LSI) through the gingival region. In one embodiment, the change in blood flow is measured by an apparatus comprising a light source and a detector for detecting transmission of light through the gingiva region of the subject.

Other features and advantages of the invention will become apparent from the following detailed description, taken in conjunction with the accompanying drawings, which illustrate, by way of example, various embodiments of the invention.

DESCRIPTION OF THE DRAWINGS

Exemplary embodiments are illustrated in referenced figures. It is intended that the embodiments and figures disclosed herein are to be considered illustrative rather than restrictive.

DETAILED DESCRIPTION

All references, publications, and patents cited herein are incorporated by reference in their entirety as though they are fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); Sambrook and Russel, Molecular Cloning: A Laboratory Manual 4th ed., Cold Spring Harbor Laboratory Press (Cold Spring Harbor, N.Y. 2012), and Rinzler and Wolff, The Encyclopedia of Dental and Oral Health (Facts on File Library of Health and Living), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

One skilled in the art will recognize many methods and materials similar or equivalent to those described herein, which could be used in the practice of the present invention. Indeed, the present invention is in no way limited to the methods and materials described.

The term "gingiva" or "gums," as used herein, contemplates the mucosal tissue that overlays the jaws with the gingival epithelium. The term "gingivitis", as used herein, contemplates an inflammation of the gingiva, often due to infection. In some embodiments, gingivitis is caused by the build-up of plaque, a sticky deposit of bacteria, mucous, food particles and other irritants, around the base of the teeth. In other embodiments gingivitis may result from injury to the gums.

The term "periodontal disease," as used herein, contemplates an inflammatory disease of the periodontium, the tissue surrounding and securing teeth to the jawbone. Examples of periodontal diseases include, but are not limited to, periodontal degeneration, gingivitis, recurrent aphthous stomatitis, non-healing wounds of the palatal mucosa or gingival mucosa, bone degeneration, or trauma to the oral mucosa or bones (e.g. tooth extraction).

As described herein, in accordance with the embodiments herein, the inventors disclose novel noninvasive methods for the characterization of gingival blood flow using Laser Speckle Imaging (LSI). In one embodiment, the technique may be laser speckle contrast analysis (LASCA) or laser speckle contrast imaging (LSCI). In one embodiment, the inventors found that there are associated changes in gingival perfusion that accompany gingivitis, and that laser speckle imaging LSI can be used to quantitatively measure those changes, thereby providing a simple method for diagnosis, prognosis, or treatment of periodontal disease. As disclosed herein, in accordance with the embodiments herein, the inventors have designed and disclosed a novel miniature dental LSI probe that is small enough to be securely positioned in the mouth, simple to use, produces accurate blood flow measurements, requires less than 5 minutes per measurement, and produces quantitative metric of disease severity to aid in diagnosis and prognosis of periodontal diseases. Laser Speckle Imaging (LSI) is a technique used to visualize and quantify blood flow. It has been employed to monitor flow in the brain, skin, and other microvasculature. To enable LSI measurements of the oral gingiva, the LSI system must be miniaturized such that it can be easily positioned and stabilized in the oral cavity. Further, to facilitate clinical usefulness, the system must also be simple to use and perform measurements relatively quickly. In one embodiment, it is important that the source and detector remain fixed/stabilized to one another as well as a specific point/location determined by the region of interest, as to eliminate motion artifact between the source, detector and the region being imaged.

In one embodiment, disclosed herein is a method of diagnosing a disease in the gingival region of an individual, comprising: quantitatively measuring blood flow or changes in blood flow in the gingival region of the individual, potentially comparing these data to that of a healthy subject, and diagnosing the disease based one of more of these quantities. In one embodiment, the disease is gingivitis. In one embodiment, the change in blood flow is measured by transmission laser speckle imaging (LSI) through the gingival region. Transmission laser speckle imaging may provide higher fidelity data compared to conventional reflection-based laser speckle imaging because the source and detector are positioned in a configuration which eliminates or greatly prohibits specularly or diffusely reflected photons from returning to the detector. Specular reflection is characterized as the mirror-like reflection that often occurs at smooth surfaces, such that the angle of incidence is equal to the angle of reflection relative to the surface normal. Diffuse reflection is characterized as the randomly oriented surface reflection that occurs on coarse surfaces such as matte glass. Diffusely reflected photons reflect in a fashion such that the angle of incidence does not necessarily equal the angle of reflection relative to the surface normal. Importantly, diffusely reflected photons do not penetrate into the sample and thus does not provide useful information from the moving light scattering particles. In one embodiment, the change in blood flow is measured by a change in speckle pattern over time. In one embodiment, the change in blood flow is measured by one or more of the following steps: illuminating the gingival region, capturing one or more laser speckle images produced by scattering of light off the gingiva, determining change in speckle pattern over time, and evaluating blood flow changes based on change in speckle patterns over time. In one embodiment, the spatial speckle contrast is performed on a single speckle image. In another embodiment, a plurality of laser speckle images is produced over time and the images are compared to determine the change in speckle pattern over time. In one embodiment, the change in blood flow is measured by an apparatus comprising a light source and a detector for detecting transmission of light through the gingiva region of the subject. In one embodiment, the change in blood flow is measured in real time. In one embodiment, the change in blood flow is associated with gingival inflammation. In one embodiment, the method further comprises treating the individual diagnosed with the disease by administering an effective amount of a medical composition for treating the disease. In one embodiment, the method further comprises one or more optics for directing the light source onto the gingiva region of the subject.

In one embodiment, disclosed herein is an apparatus, comprising: a light source and a detector for detecting transmission of light through the gingiva region of the subject. In one embodiment, the detector quantitatively measures changes in gingival perfusion and/or blood flow. In one embodiment, the method further comprises one or more optics for directing the light source onto the gingiva region of the subject. In one embodiment, the light source comprises a laser diode. In one embodiment, the detector comprises a camera. In one embodiment, the apparatus is adapted to fit within the mouth of the subject. In one embodiment, the apparatus is adapted to fit in place within the mouth of the subject by custom molds. In one embodiment, the custom molds are from dental putty.

Further, as will be readily appreciated by those skilled in the art, the mechanism for aligning the source and detector within the oral cavity is not limited to dental putty—other techniques such as, for example, dental adhesives, clamps, and other methods known in the art of fixation of source and detector within the oral cavity may be used. A lack of fixation of source (example, laser) and/or detector (example, camera) to a point within the oral cavity causes motion artifact, and is a limiting factor towards usable data within a practical dental setting.

In one embodiment, disclosed herein is a method of determining an efficacy of a gingivitis treatment in a patient, comprising: measuring blood flow through the gingival region of a patient at the start of a treatment; measuring blood flow through the gingival region of the patient at the end of a treatment; and determining efficacy of the treatment based on the presence of an increase in blood flow at the end of the treatment relative to the start of the treatment. In one embodiment, blood flow is measured by one or more of the following steps: illuminating the gingival, capturing a plurality of laser speckle images produced by scattering of light off the gingiva, determining change in speckle pattern over time, and evaluating blood flow changes based on change in speckle patterns over time. In one embodiment, the change in blood flow is measured by transmission laser speckle imaging (LSI) through the gingival region. In one embodiment, the change in blood flow is measured by an apparatus comprising a light source, one or more optics for directing the light source onto the gingiva region of a subject, and a detector for detecting transmission of light through the gingiva region of the subject.

As further described herein, measuring gingival blood flow can be important because it is a direct indicator of gingival inflammation. In some embodiments, the present disclosure provides an early marker for onset and treatment response in patients with gingivitis. Currently, clinical probing indices are used to identify and quantify gingivitis activity and quiescence. Diagnoses acquired using these indices lag by several days behind the pathological status of the tissues. In another embodiment, the inventors provide a real time detection of gingival blood flow. In one embodiment, the methods and apparatus described herein enables real time measurement of blood flow in the gingiva, thereby allowing better treatment outcomes.

In one embodiment, the present disclosure provides a method of evaluating the gingival region, comprising: measuring blood flow by transmission laser speckle imaging through the gingival region. In another embodiment, the method is useful for diagnosing gingival inflammation. In another embodiment, the method is useful for diagnosing an onset of gingivitis in a patient. In another embodiment, the method is useful as a marker for treatment response in patients. In some embodiments, the method provides a real time tool for evaluating blood flow characteristics in the gingiva. In other embodiments, the method is useful for the diagnosis, prognosis, or treatment of a periodontal disease. In some embodiments, the method further comprises: (a) illuminating the gingiva with light from a coherent light source; (b) capturing, using a camera, a plurality of laser speckle images produced by the scattering of the light off of the gingiva; (c) determining change in speckle pattern in space or over time from the one or more laser speckle images to; and (d) evaluating blood flow characteristics in the gingiva based on the dynamics of the speckle pattern in space, time, or both. As described herein, the present invention is in no way limited to changes in speckle pattern over time—changes also refer to those changes that occur within a single image.

In another embodiment, the present disclosure provides an apparatus comprising: (a) a coherent light source; (b) a detector for detecting transmission of the at least partially coherent light through the gingiva. In one embodiment, the apparatus is useful for diagnosing gingival inflammation. In some embodiments, the apparatus is useful for diagnosing an onset of gingivitis in a patient. In some embodiments, the apparatus is useful as a marker for treatment response in patients. In one embodiment, the apparatus provides a real time tool for evaluating blood flow characteristics in the gingiva.

In one embodiment, provided herein is a method for diagnosing or prognosing gingivitis or gingival inflammation in a patient, comprising: (a) evaluating blood flow characteristics in the patient comprising measuring blood flow by transmission laser speckle imaging through the gingival region; (b) comparing the blood flow of the patient to that of a healthy individual without gingivitis or gingival inflammation; and (c) diagnosing or prognosing gingivitis or gingival inflammation in the patient if the blood flow in the patient's gingiva is different from the blood flow in the healthy individual's gingiva. In one embodiment, increased perfusion is indicative of inflammation. In another embodiment, increased perfusion is indicative of more healthy teeth and gingiva compared to teeth and gingiva where insufficient blood perfusion might be present.

In one embodiment, provided herein is a method for determining an efficacy of a gingivitis or gingival inflammation treatment in a patient, comprising: (a) evaluating blood flow characteristics in the patient, comprising measuring blood flow by transmission laser speckle imaging through the gingival region at the start of the treatment and at the end of the treatment; (b) comparing the blood flow characteristics in the gingiva at the start of the treatment and at the end of the treatment; and (c) determining that the gingivitis or gingival inflammation treatment is efficacious if the blood flow in the patient's gingiva is different at the end of treatment compared to the blood flow in the beginning of the treatment.

In some embodiments, provided herein is a method for treating gingivitis or gingival inflammation, comprising: (a)

evaluating blood flow characteristics in the patient comprising measuring blood flow by transmission laser speckle imaging through the gingival region; (b) comparing the blood flow of the patient to that of a healthy individual without gingivitis or gingival inflammation; (c) diagnosing gingivitis if the blood flow in the patient's gingiva is different from (increased or decreased perfusion) the blood flow in the healthy individual's gingiva; and (d) treating gingivitis or gingival inflammation with gingivitis or gingival inflammation medicine.

As further described herein, the inventors designed a miniature dental LSI probe with the following features: small enough to be securely positioned in the mouth, simple to use, produces accurate blood flow measurements, requires less than 5 minutes per measurement, and produces quantitative metric of disease severity to aid in diagnosis and prognosis.

As further disclosed herein, the inventors created an LSI system that uses components small enough to be mounted completely or mostly within the oral cavity. In accordance with one or more embodiments herein, this was accomplished by using a miniature CMOS camera (approximately one cubic millimeter) and a compact laser diode package that could be fixed in place within the mouth using custom molds fabricated from dental putty. Using these molds, the laser diode and camera were be mounted on the buccal and lingual side of the gingiva and used to perform LSI in a trans-illumination geometry.

As further disclosed herein, the inventors performed in vitro experiments to assess the stability, precision, and repeatability of our device to collect speckle contrast data. Additionally, they performed an in vivo study using this novel system to measure perfusion in the interdental papilla and marginal gingiva of the upper canines and incisors in subjects diagnosed with mild to moderate gingivitis. Measurements were acquired at baseline and during three weeks of gingival home-care to determine whether LSI measurements of gingiva correlate to standardized clinical metrics of gingivitis severity.

In one embodiment, the present disclosure provides a laser speckle imaging device comprising a miniature camera and a small laser diode, where the miniature camera and the laser diode are fixed in place within a patient's mouth using custom molds fabricated from dental putty. In one embodiment, the device fits snuggly around the patient's teeth inside the patient's mouth. In one embodiment, the laser diode and miniature camera are mounted on the buccal and lingual side of the gingiva. In one embodiment, the device performs LSI in trans-illumination geometry. In one embodiment, the device is designed for use in a patient's mouth. In one embodiment, the device quantitatively measures changes in gingival perfusion. In one embodiment, the device accurately measures blood flow in the gingiva. In one embodiment, the device requires less than five minutes per measurement. In one embodiment, the device is capable of diagnosing, prognosing, or treating a periodontal disease. In one embodiment, the device provides a quantitative metric of a periodontal disease severity to aid in diagnosis, prognosis or treatment of the disease. In one embodiment, the miniature camera and the small laser diode are fixed in place inside the mouth using custom molds fabricated from dental putty.

Embodiments of the present disclosure are further described in the following examples. The examples are merely illustrative and do not in any way limit the scope of the invention as claimed.

EXAMPLES

Example 1

Assessment of Gingival Blood Flow Using Transmission LSI

In one embodiment, the inventors demonstrated that LSI could be performed in a transmission geometry through the gums/gingiva. While LSI was used previously through the tooth to assess pulpal vitality, the successful implementation of transmission LSI through the gingiva was unexpected and surprising because the measurement thickness is larger, the degree of tissue blood flow/perfusion is greater, and the optical properties of the gingiva are quite different from that of the tooth.

Figure 1:
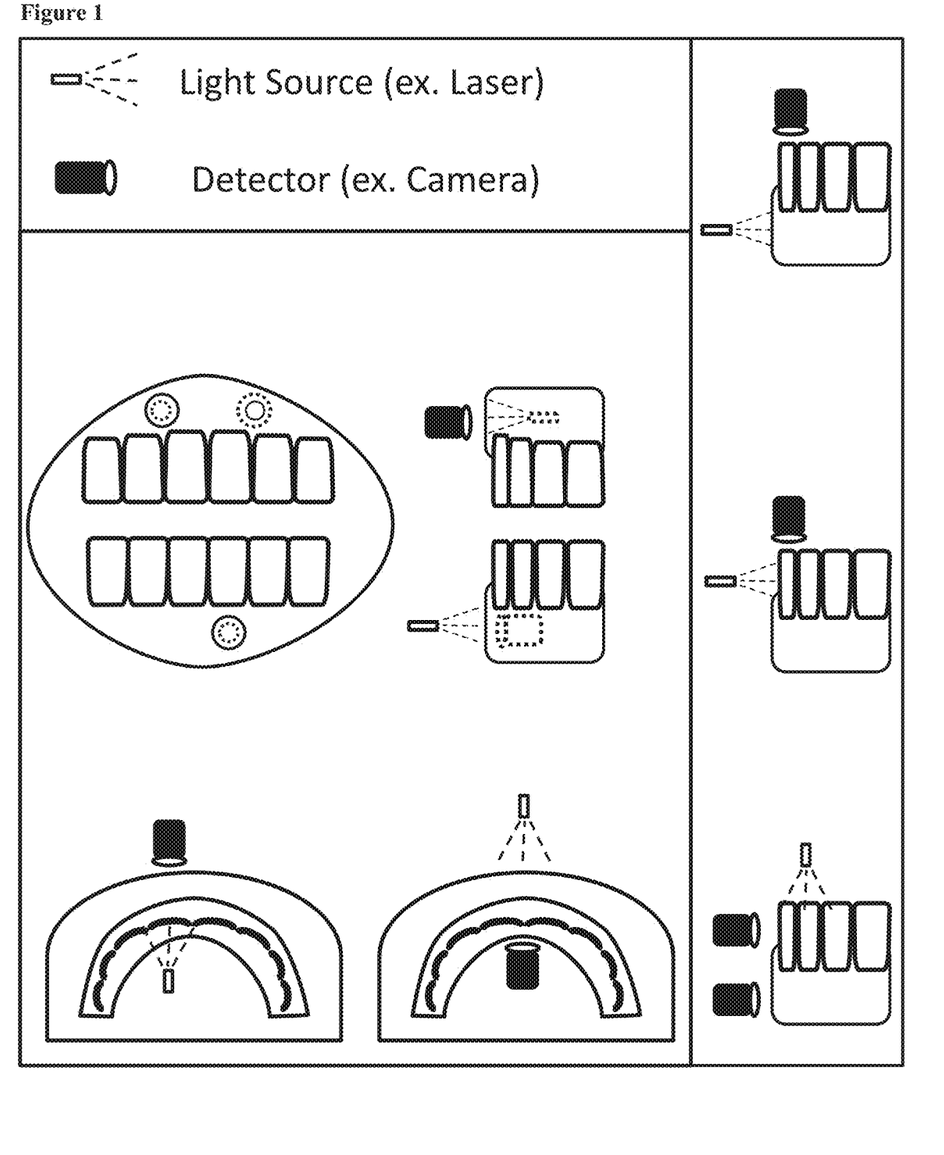
FIG. 1 depicts, in accordance with the embodiments herein, one embodiment of the disclosure illustrating the application of transmission LSI through the gingiva.

FIG. 1 provides one example of transmission LSI through the gingiva. FIG. 1 demonstrates just one of many potential transmission configurations, and it emphasizes just one region of the gingiva that can be targeted for the purpose of demonstration. The inventors foresee measuring gingival flow within the entire gingival region. In one embodiment, the device places the source and detector at different positions, as needed to properly assess gingival blood flow.

Example 2

Comparative Benefits and Advantages

Devices currently available for measuring gingival blood flow give inconsistent values due to pressure artifact, limited penetration depth, and small region of interrogation. These limitations are overcome by using the apparatus and methods disclosed herein. The measurement of gingival blood flow using transmission LSI provides consistent and reliable values due to deeper penetration on larger gingival region of interrogation.

Furthermore, LSI is superior to photoplethysmography (PPG), another known optical measurement technique, with regards to sensitivity and the ability to quantify blood flow rather than changes in blood volume. Furthermore the principles of PPG can be carried out using an LSI setup, while the reverse is not true.

Example 3

LSI Technique

There are a number of challenges associated with creating compact imaging system for use in the oral cavity. First, each component must be small enough to fit relatively comfortably in the mouth. Second, all electrical components must be housed to keep them dry and free of saliva. Third, they must be able to be sanitized between patient measurements. Fourth, without affixing the imaging components to the teeth or gingiva, significant motion artifact may be introduced, thereby making hand-held systems or external imaging systems untenable. Previous studies published on the ability to measure pulsatile blood flow in the teeth using a fiber bundle-based LSI device which required the patient to hold their head steady while biting on a laser fiber. However, this system was difficult or uncomfortable for most patients and it is difficult to deploy in a confined clinical setting.

In one embodiment, a novel LSI system was created, which uses components small enough to be mounted completely or mostly within the oral cavity. This was accomplished by using a miniature CMOS camera (approximately one cubic millimeter) and a compact laser diode package that was be fixed in place within the mouth using custom molds fabricated from dental putty. Using these molds, the laser diode and camera were mounted on the buccal and lingual side of the gingiva, and it was used for performing LSI in a trans-illumination geometry. It is important that the source and detector remain fixed to a specified point as to eliminate motion artifact between the source, detector and the region being imaged.

Using this system, the inventors performed in vitro experiments to assess the stability, precision, and repeatability of the novel LSI device to collect speckle contrast data. Additionally, an in vivo study was performed using the novel LSI system to measure perfusion in the interdental papilla and marginal gingiva of the upper canines and incisors in subjects diagnosed with mild to moderate gingivitis. Measurements were acquired at baseline and during three weeks of gingival home-care to determine whether LSI measurements of gingiva correlate to standardized clinical metrics of gingivitis severity.

Example 4

Device Design

The compact camera used in the LSI system was an Awaiba NanEye CMOS camera (CMOSIS, Raleigh, N.C.). It is equipped with an f/#2.7 lens, which had an 8-75 mm depth of focus and utilized a rolling shutter during image acquisition. The entire package (camera and lens) measured 1.0×1.0×1.7 mm, which allowed for comfortable intraoral use. The camera had maximum sensitivity between 600-700 nm, which was optimal for the light source (7 mW 655 nm single longitudinal mode, 3.3 mm diameter TO can package laser diode (Roithner LaserTechnik GmbH, Vienna, Austria)). The NanEye had a 4-pin connection to a USB2 evaluation board that connects to a standard PC running provided software (Awaiba Viewer v2.15.2.1). To protect the camera and camera wiring, it was secured in a 3D-printed casing using silicone glue. This case also provided additional material with which to stabilize the camera during use. The laser diode was powered by a laser diode controller 240C (ThorLabs Inc, Newton, N.J.) set to a current limit of 30 mA. The diode was housed within a custom machined cylindrical casing fabricated from delrin. This casing also contained an aluminum heat sink to aid in diode stabilization.

Example 5

Image Processing

During data collection, "color reconstruction" and "reduce processing" options in the Awaiba Viewer software were turned off and on, respectively, in order to ensure raw data was collected. The proprietary Awaiba Viewer software saves data as .avi files, which were converted to a .tiff image sequence using ImageJ software (NIH), followed by computing speckle contrast maps from each image using MATLAB (MathWorks, Natick, Mass.). Speckle contrast was calculated as the standard deviation over the mean intensity in a given region of pixels. The inventors computed both a spatial contrast value using a 7×7 sliding window, as well as a rolling temporal contrast value by computing temporal contrast across each pixel of subsequent 4 frame sequences (i.e.: frames 1:4, 2:5, 3:6, etc). The contrast was averaged within an user-selectable ROI (pertaining the gingival tissue of interest) and computed a speckle flow index (SFI) value, $\frac{1}{2}TK^2$, where T is the exposure time and K is the speckle contrast.

Example 6

Static In Vitro Device Validation

To test the stability of the NanEye camera and the laser diode used during in vivo data collection, a static PDMS phantom ($\mu_s'=1$ mm$^{-1}$) was measured over a period of time using the NanEye camera to quantify the changes in speckle contrast not resulting in movement or flow. Image sequences were collected at 42 fps. An ROI was chosen to compute averaged spatial speckle contrast. This measurement was performed as several different intensities spanning the dynamic range of the NanEye camera to determine the dependence of illumination intensity on measured speckle contrast.

Example 7

Dynamic In Vitro Device Validation

In vitro experiments were performed to validate the NanEye camera for use in LSI. A flow phantom was fabricated using a polydimethylsiloxane (PDMS) with titanium dioxide added to give a reduced scattering coefficient ($\mu_s'$) of 1 mm$^{-1}$, which is typical of tissue at 655 nm. A glass microchannel with diameter 650 µm was embedded in the surface of the PDMS, and 1% Intralipid (Baxter Healthcare, Deerfield, Ill.) was infused at different speeds (0.5 mm/s, 1.0-7.0 mm/s by 0.5 mm/s increments, 15 mm/s) using a syringe pump (Harvard Apparatus, Holliston, Mass.).

In vitro validation imaging was performed by comparing the NanEye camera and a monochrome Chameleon camera (Point Grey, Richmond, BC, Canada), a commonly used research grade CCD camera. A 150 mW 808 nm diode laser (Ondax Inc, Monrovia, Calif.) with a ground glass diffuser was used to illuminate the flow phantom, and collected sequences of images with the NanEye and Chameleon cameras. Images were collected using an exposure time of 2 ms, and a frame rate of 42 fps and 15 fps for the NanEye and Chameleon cameras, respectively. Spatial speckle contrast was computed in a 10×10 or 30×30 pixel region (NanEye/Chameleon) within the center of the microchannel, for 25 frames, and then averaged to improve the signal to noise ratio.

Example 8

In Vivo Data Collection Setup

Prior to imaging each subject, a custom-fit impression mold was created of each patient's upper teeth and gingiva spanning the upper right to left premolars. All measurements were taken from the interdental papilla above the upper canines and incisors. The molds were made of polysiloxane Dental Putty (Coltene/Whaledent Inc, Cuyahoga Falls, Ohio) combined with a ~6 cm stripe of Activator gel. The Dental Putty and Activator were mixed by hand for ~60 s and then formed into a rectangular block of approximately 1.5×2×7 cm. An impression of the patient's teeth was created into the block of dental putty, while pressing firmly to create a close fit around the teeth and gingiva. The putty was held in place until it hardened (~2 min).

To enable mounting of the encased camera and laser diode, holes were drilled into the buccal and lingual sides of the mold such that a straight light path was created between the light source and the detector for maximum light throughput in a transillumination geometry. The camera and laser diode housings were inserted into the drilled holes and were held rigidly in place via friction. Using this system, the mold could be repeatedly inserted and removed from the patient's mouth while maintaining a similar imaging location for every measurement. Repeatability of imaging locations was critical for longitudinal study of gingival blood flow dynamics.

The encased camera and laser diode were wrapped with disposable Cover-All barrier film (Kerr TotalCare, Orange, Calif.) before use on each subject to prevent cross-contamination. Additionally, they were additionally sanitized using 70% alcohol swabs between uses.

Example 9

In Vivo Exposure Time Selection

To aid in the selection of an exposure time to be used during LSI which would maximize sensitivity to blood flow changes during the cardiac cycle, the inventors used the setup described above to measure gingival blood flow while varying the Naneye exposure time from 2 to 23 ms (corresponding to exposure settings in Awaiba Viewer of 25, to 249 is 24 or 25 unit steps). 30 seconds of data was collected at each exposure time with minimal perturbation introduced between measurements to minimize vasoconstriction or vasodilation-mediated changes in blood flow during the measurement period. Spatial speckle contrast was computed from each data as performed above and the average change in K between systole and diastole was computed. This metric was used quantify the sensitivity of the imaging system to physiologically relevant changes in the blood flow at various exposure time.

Example 10

In Vivo Device Validation

To ensure that changes in gingival blood flow could be detected, the speckle flow index was measured while manually perturbing blood flow. Blood flow perturbation was achieved by applying manual pressure to the back of the Naneye camera housing, which induced blanching in the marginal gingiva between the upper incisors. Measurements were performed by acquiring baseline blood flow measurements for two minutes, followed by a one minute of pressure-induced gingival blanching occlusion, and then a two minute recovery period. Baseline flow was measured in four regions of the gingiva, moving progressively from the interdental papilla between the upper incisors to the marginal gingiva, to the attached gingiva, and finally to the alveolar mucosa.

Example 11

In Vivo Device Repeatability

To quantify the repeatability of the novel LSI device to measure the same region each time the imaging system is inserted into the oral cavity, the inventors acquired eleven measurements (~20 s each) on a single patient. Between each measurement, the imaging system was removed and reinserted. Collected image sequences were used to compute spatial contrast within an ROI approximately 61×61 pixels in dimension corresponding to the interdental papilla above the upper canines and incisors. Speckle contrast across each image sequence was averaged the average speckle contrast for each measurement was used to compute standard deviation or coefficient of variation.

To quantify the repeatability of the novel LSI system longitudinally over the course of several days, multiple measurements were acquired in different gingival locations on a healthy subject over nine days. Each day, the inventors acquired six ~30 s measurements from three locations of one patient: (1) interdental papilla between the upper left canine and incisor, (2) marginal gingiva directly above the cementoenamel junction of the upper left incisor, (3) approximately 1 mm above the cementoenamel junction above the upper left incisor. As above, the average spatial contrast values was computed in a 61×61 pixel ROI, and the coefficient of variation (standard deviation/mean) was computed for each location during the measurement trial period.

Example 12

In Vivo Experimental Measurements

Patient measurements were taken for 3 minutes at 30 frames per second to ensure stability of the signal. Patient measurements were taken with an exposure time of 5 ms, a gain of 3, and an offset of either 1 or 2 depending on the baseline intensity. Any measurements with intensity below 40 counts were discarded. Before any laser speckle contrast imaging data was collected, the patient was given a visual examination by a certified dentist to grade their plaque index and gingival inflammation index.

Laser speckle contrast was calculated in a 51×61 pixel region of interest (ROI). The average SFI over the first 2900 frames (~96 s) was computed to compare patient measurements.

Example 13

Results

Figure 2:
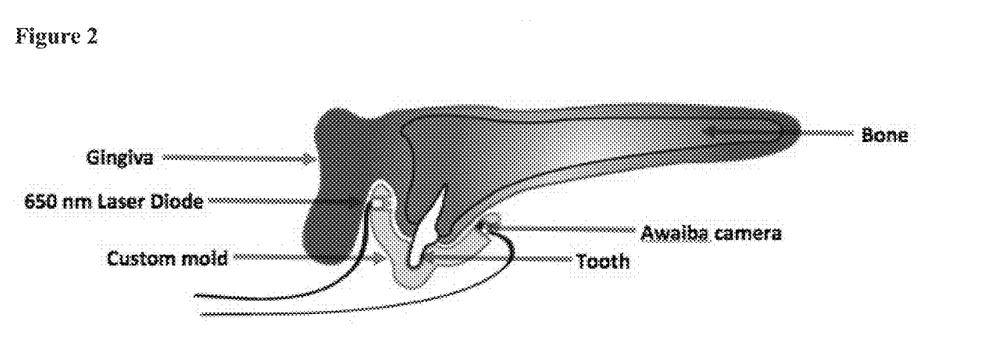
FIG. 2 depicts, in accordance with the embodiments herein, one embodiment of the device disclosed herein.

One embodiment of the novel device built by the inventors to acquire laser speckle images of the gingiva is illustrated in FIG. 2. A series of transilluminated images of the marginal and attached gingiva were collected using a miniature camera placed on the labial side of a custom-fit dental putty mold. The speckle pattern was generated using a near-infrared laser diode on the lingual surface of the mold, which had good depth penetration into perfused tissue. The mold fit securely around the upper anterior teeth, which held the camera and laser diode fixed relative to each other and in the same location every time the mold was inserted. This was important to minimize motion artifacts, which inherently plague many LSI devices, as well as to ensure measurements were taken in the same location, which was important because blood flow in the oral cavity has significant variance due to physiology.

Figure 3:
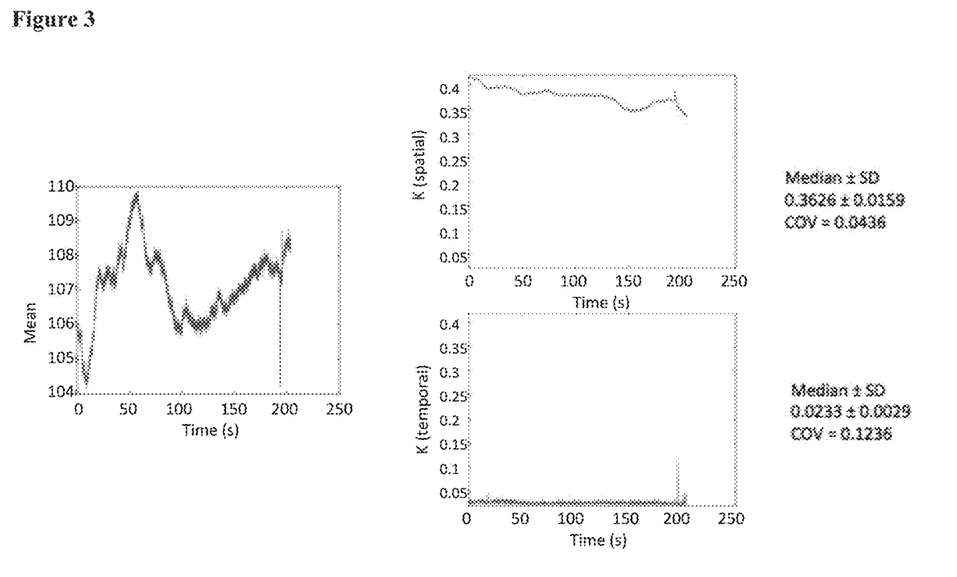
FIG. 3 depicts, in accordance with the embodiments herein, stability of laser diode/Awaiba camera.

A static phantom over ~200 s was measured to monitor the stability of the intensity of the laser diode and the contrast in images collected using the NanEye camera and AwaibaViewer software. The intensity of the laser diode remained stable within several counts [FIG. 3, left]. The power output of the laser diode was measured over time to demonstrate that it remained stable over time. This illustrated that the aluminum heat sink constructed was sufficient to stabilize the diode. The spatial and temporal contrast was measured over the 200 s and found that the coefficient of variation was 0.0436 and 0.1236 respectively [FIG. 3 top right, bottom right]. In one embodiment, the inventors observed more fluctuations in temporal contrast than spatial, both in vitro and in vivo. In one embodiment, these in vivo fluctuations represent physiological variations in flow. In another embodiment, these in vivo fluctuations are due to camera noise. In one embodiment, the variation in what should be a stable in vitro measurement on a static phantom implies that using spatial contrast is more reliable for clinical experiments.

Figure 4:
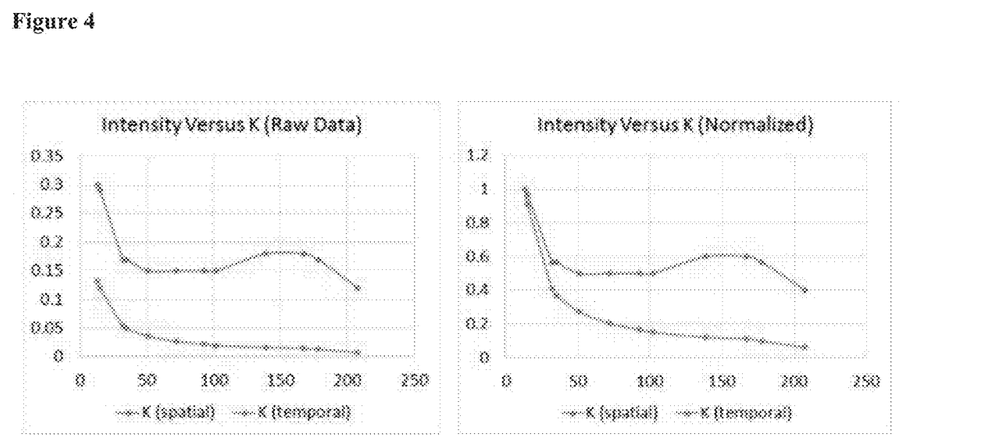
FIG. 4 depicts, in accordance with the embodiments herein, the need for more than 20 intensity counts.

The intensity versus spatial and temporal contrast was measured [FIG. 4 left, right] in a static phantom for the NanEye camera by changing the current supplied to the laser diode. In vivo, contrast values became unpredictable when operating the device with low intensity counts. Both temporal and spatial contrast spiked when the intensity dropped below ~40 counts. Spatial contrast increased slightly for intensity counts between ~140-175. In one embodiment, the inventors aimed to have intensity values between 60-120 counts for the in vivo patient measurements.

Figure 5:
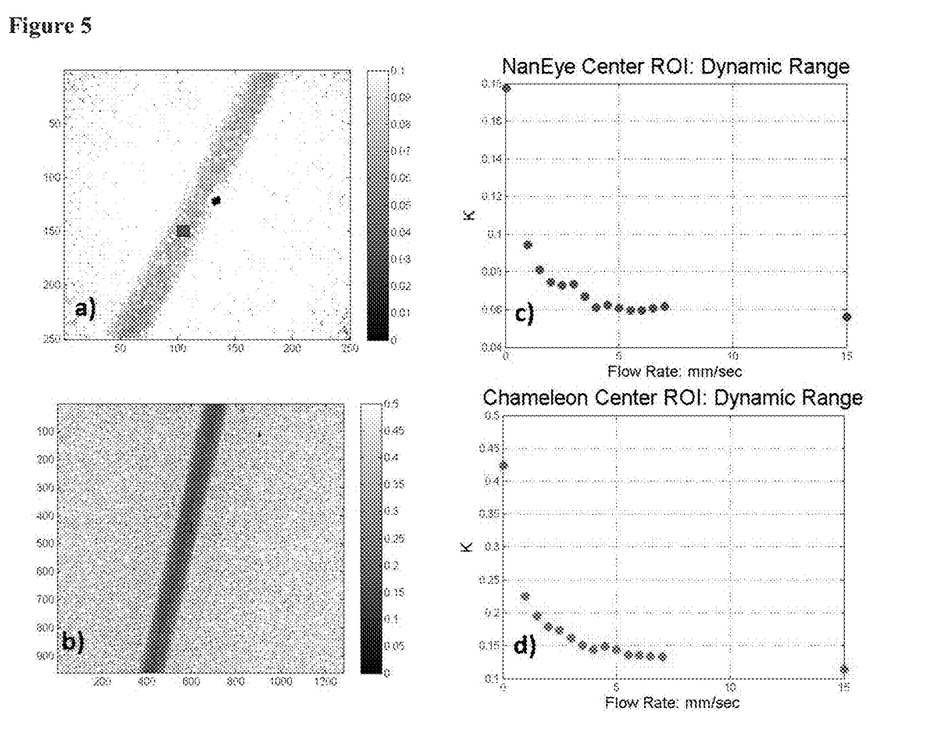
FIG. 5 depicts, in accordance with the embodiments herein, contrast values at different flow speeds calculated from images taken with the NanEye versus the Chameleon camera.
Figure 6:
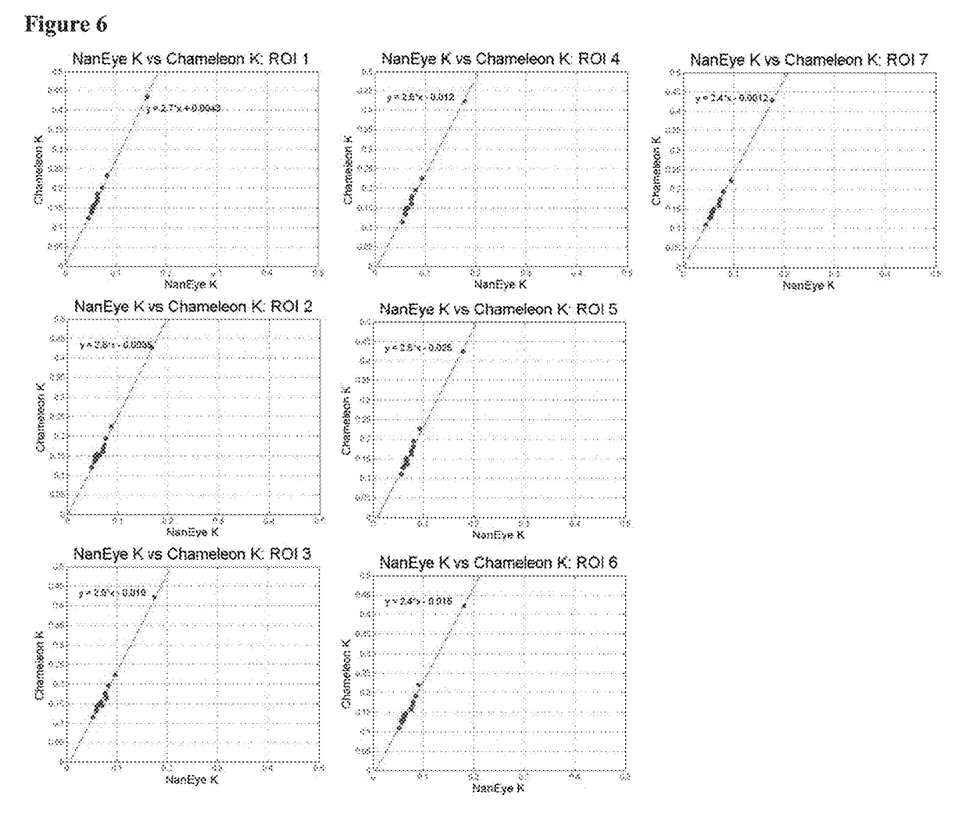
FIG. 6 depicts, in accordance with the embodiments herein, comparison of Awaiba and Point Grey cameras.

In one embodiment, the inventors compared in vitro flow phantom data collected with a research grade LSI system to data collected with the Awaiba NanEye camera to ensure the miniature camera was capable of collecting data with a sufficient dynamic range, at a high enough resolution, and with limited artifacts due to the built-in lens system. The inventors measured the speckle contrast of flow in a glass microcapillary tube at a range of speeds (FIG. 5). The image from the NanEye camera had lower resolution compared with the Chameleon (FIG. 5a vs 5b), which resulted in rougher boundaries and a grainer image. There was also some barrel distortion present near the edges of the image taken with the NanEye camera due to the small lens. This did not affect the novel device, because data was collected from the center ~60×60 pixel region. In this region, the inventors demonstrated that contrast decays exponentially with flow speed, as predicted by speckle theory [FIG. 5c, 5d]. The dynamic range for the NanEye [FIG. 5c] was ~0.12 for the flow speeds that were tested, whereas it was ~0.3 for the Chameleon [FIG. 5d]. A linear trend was observed ($R^2$=0.993) between contrast values at different flow speeds calculated from images taken with the NanEye versus the Chameleon Camera [FIG. 6]. This was important because it demonstrated that even though the dynamic range was lower for the NanEye, it still maintained the same contrast response to flow speed as a research grade camera.

Figure 7:
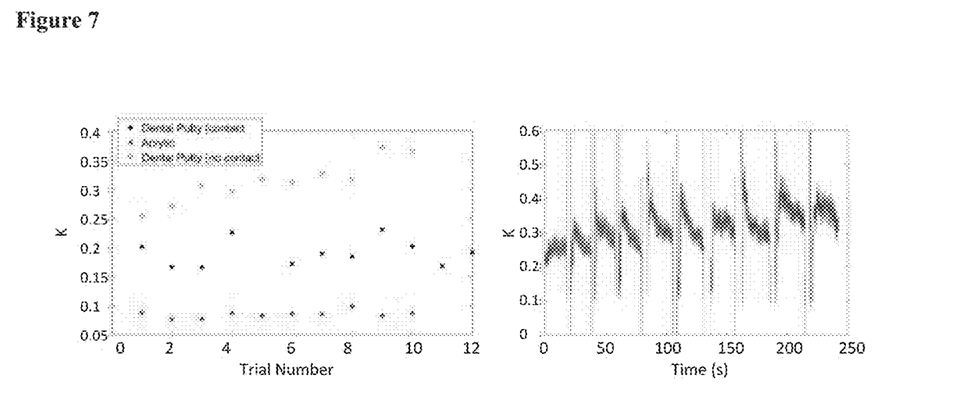
FIG. 7 depicts, in accordance with the embodiments herein, stability of repeated measurements (single patient).

Multiple sets of data were taken on a single patient while removing and replacing the mold between measurements to test the ability of the novel device to repeatably measure speckle contrast. The coefficient of variation was measured between eleven measurements FIG. 7 using the spatial and temporal algorithms. This data demonstrated that the device was capable of imaging the same location in the gingiva and obtaining precise contrast values across multiple uses.

Figure 8:
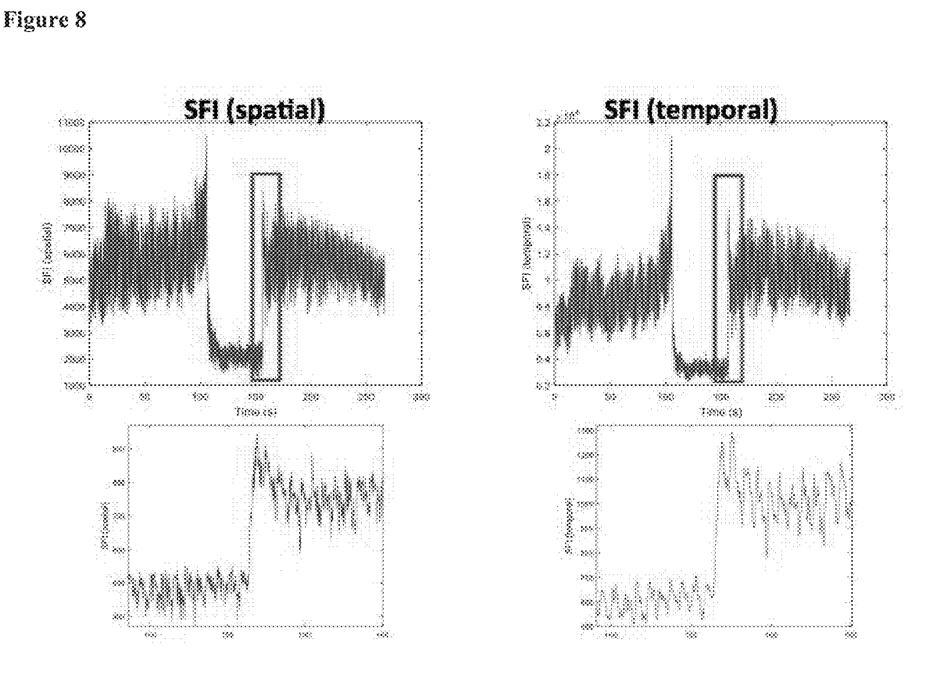
FIG. 8 depicts, in accordance with the embodiments herein, ability to detect induced changes in flow/greater dynamic range of temporal contrast.
Figure 9:
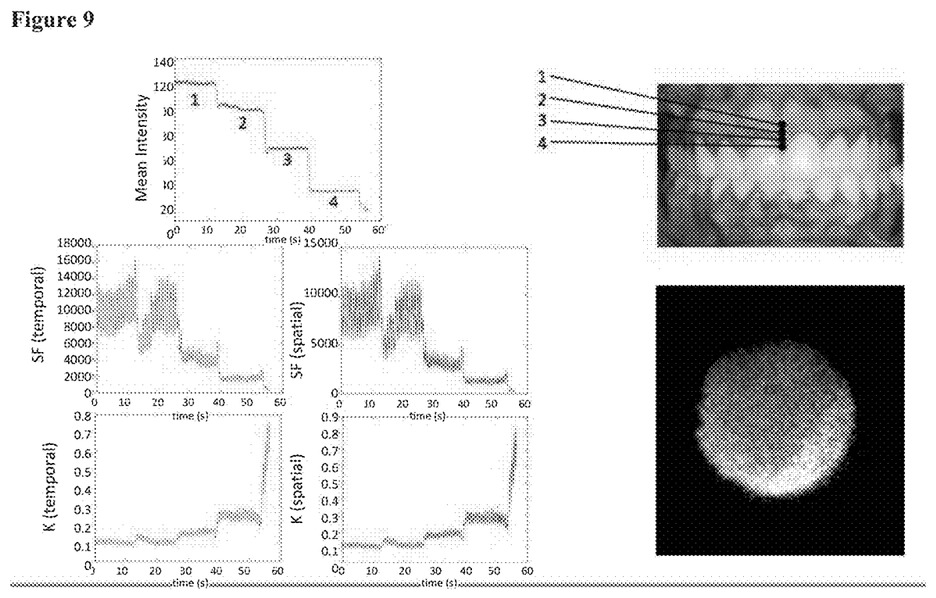
FIG. 9 depicts, in accordance with the embodiments herein, changes in contrast due to measurement location

To ensure that the device could differentiate between induced changes in gingival blood flow, the inventors performed a mechanical occlusion of the vessels in the marginal gingiva above the upper incisors of a healthy subject. The inventors could distinguish a clear difference in both spatial and temporal speckle flow index between normal use of the device and during application of pressure to impede blood flow [FIG. 8 top left, top right]. Additionally, there could resolve the differences in blood flow during each heartbeat [FIG. 8 bottom left, bottom right]. The signal to noise ratio is higher for temporal because of the smoothing effect of measuring over multiple frames. A higher change was seen in SFI from the occlusion to the return of normal blood flow using the temporal algorithm ($\Delta SFI_{temporal}$=630) as compared to the spatial algorithm ($\Delta SFI_{spatial}$=470). This indicated that temporal SFI has a greater dynamic range and sensitivity to physiological changes in flow. The intensity and contrast was measured in four locations of the gingiva between the upper incisors of a healthy subject: the interdental papilla, the marginal gingiva, the attached gingiva, and the alveolar mucosa. The intensity decreased relatively linearly as the location was moved further away from the interdental papilla [FIG. 9]. This was probably the thickness of the area being transilluminated was increased, therefore there was more photon absorption and less light is arriving at the detector. There was a corresponding increase in contrast with the move up the gingiva [FIG. 9]. This was likely because there was static scattering from the bone and the roots of the teeth with the move away from the interdental papilla, which causes an increase in contrast. The data is illustrated in table 1.

TABLE 1

Stability of repeated measurements over several days

| Subject | $<K_{spatial}>$ | $<K_{temporal}>$ | $COV_{spatial}$ | $COV_{temporal}$ |
| --- | --- | --- | --- | --- |
| CR1 | .1456 | .0158 | .0085 | .0534 |
| CR2 | .1471 | .0172 | .0085 | .0652 |
| CR3 | .1470 | .0181 | .0148 | .1082 |
| BY2 | .1469 | .0180 | .0111 | .0824 |
| BY3 | .1475 | .0182 | .0037 | .0723 |

Figure 10:
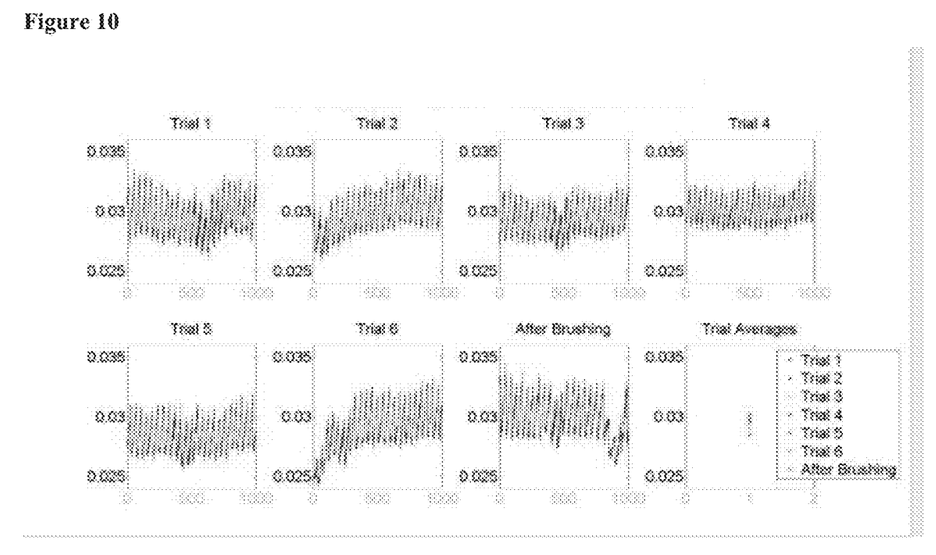
FIG. 10 depicts, in accordance with the embodiments herein, stability of repeated measurements (multiple days).

In one embodiment, the inventors measured spatial and temporal contrast in two healthy subjects in multiple locations on the gingiva over a period of days in order to measure the stability of the device to obtain repeatable contrast values across multiple longitudinal measurements, and physiological variations in flow from day to day. Very low coefficients of variation were observed in spatial contrast (less than 0.02) for five and six days of measurements in a seven and nine day period respectively [FIG. 10]. The variation in temporal contrast was slightly higher (0.05-0.11 coefficient of variation). The higher variation in temporal contrast is in line with similar observations in vitro [FIG. 5d]; this is likely due to camera noise rather than temporal fluctuations in the light source. No significant variations in contrast were seen between gingival locations between measurements taken in the interdental papilla versus the marginal or attached gingiva above the cementoenamel junction (COV patient CR: 0.0057 (spatial), 0.0680 (temporal)).

Figure 11:
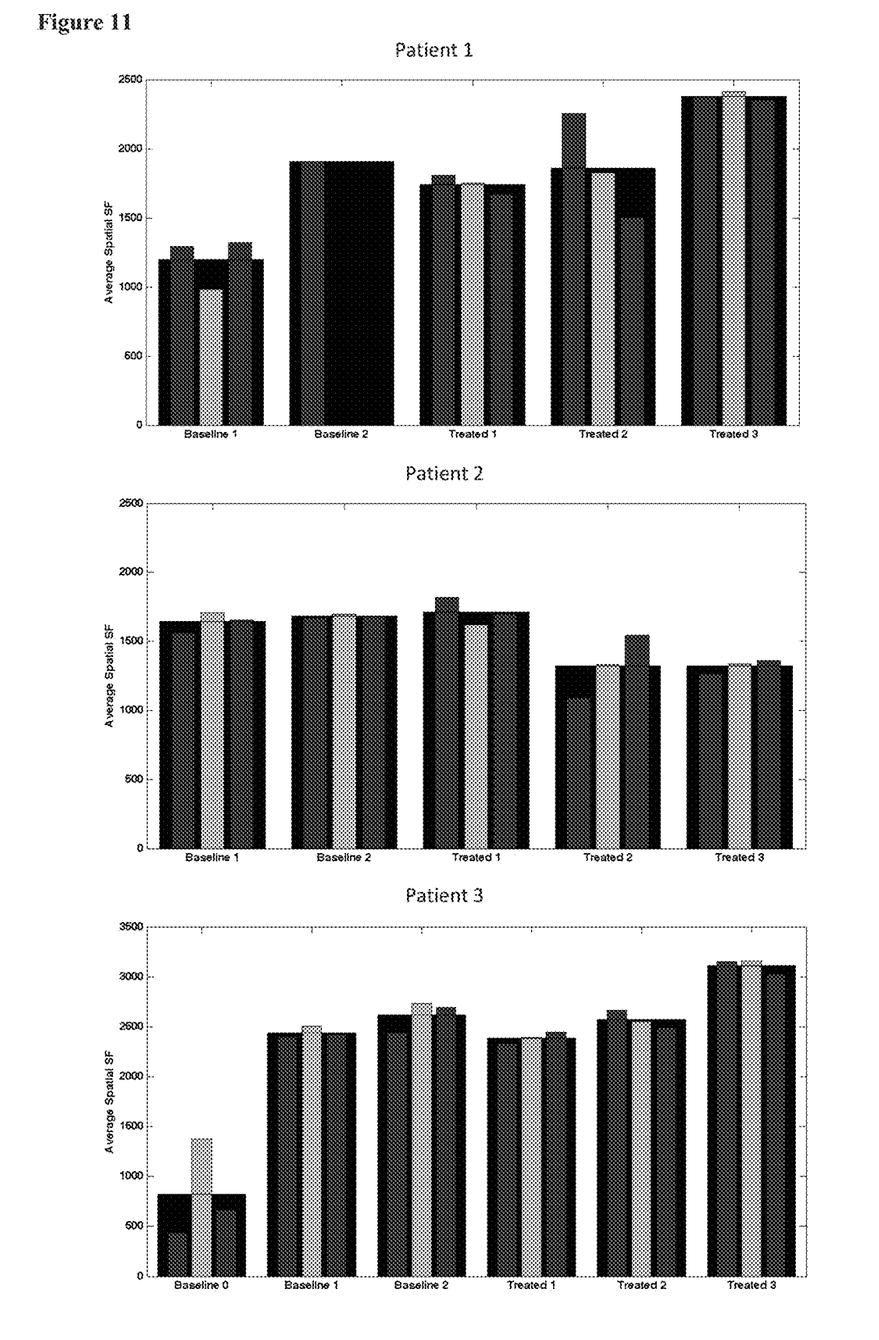
FIG. 11 depicts, in accordance with the embodiments herein, patient data.

The inventors took measurements over five weeks in patients who were undergoing treatment for mild to severe gingivitis. Three 180 s measurements were taken in each patient every week; there were two to three weeks of baseline measurements where patients were asked to maintain their standard oral health care routine. The last three weeks the patients were taught proper brushing technique, and given toothbrushes, Colgate Total toothpaste and mouthwash. The average spatial SFI for each measurement is shown [FIG. 11, colored bars], as well as the average for the visit (black bar). The SFI values for each of the three measurements in a given visit were consistent, which demonstrated the repeatability of the novel device disclosed herein.

Example 14

Experimental Results

The experiments disclosed herein demonstrated the feasibility and stability of a miniature laser speckle imaging device designed for use in the mouth. The device fits snuggly around a patient's teeth, and securely holds a miniature camera and small laser diode in place to transilluminate the gingiva [FIG. 2].

A number of in vitro and in vivo experiments were performed to validate the system's ability to maintain stability and repeatability. The stability of the laser diode was measured using both a power meter and the Awaiba NanEye camera to ensure that fluctuations in intensity had a coefficient of variation below 0.05 [FIG. 3]. In order to achieve stable spatial and temporal contrast values using the device, the inventors operated in the 60-120 count intensity regime [FIG. 4]. Additionally, the optimal exposure time for the device to be sensitive to physiological changes in flow was ~5 ms, which was less than previous clinical LSI systems. A comparison of the instantly disclosed device and a laboratory grade LSI system demonstrated a linear relationship between contrast values from each system as a function of flow speed [FIG. 5, 6]. A lower dynamic range was not observed with the miniature oral device, which was probably due to the lower quality of the camera.

The inventors collected in vivo data on healthy subjects to demonstrate the ability to detect changes in blood flow and perfusion in the gingiva. During a pressure-induced occlusion of the gingival vasculature, a sharp decrease in both spatial and temporal speckle flow index was detected [FIG. 8]. This was consistent with expectations of decreased flow during an occlusion. A decrease in SFI was observed with a change in measurement location from the interdental papilla towards the marginal and attached gingiva [FIG. 9]. While the locational decrease was likely due to less overall perfusion or due to the increase in thickness of the region being measured. There was a corresponding decrease in intensity, which indicated that not as much light was reaching the detector. These changes in SFI also may be due to an increase in spatial scattering from the maxilla or the roots of the incisors.

In vivo measurements were performed on healthy subjects to ensure that the device could obtain repeatable contrast values across multiple measurement sessions. The data demonstrated that the device could be removed and replaced while maintaining precise measurements of spatial and temporal contrast in the gingiva [FIG. 7]. Additionally, data collected in a subject longitudinally showed consistent contrast values [FIG. 10]. This indicated that that the device was capable of repeatedly measuring the same location in the gingiva, and physiological changes in flow from day to day did not cause significant changes in contrast value. In one embodiment, this data illustrated that LSI could be used as a diagnostic aid or a tool for the assessment of changes in gingival health over time.

Measurements were also performed in patients that were being clinically evaluated and counseled for gingivitis. Consistent results were obtained in each of the three measurements acquired per patient visit, which corresponded to the previous in vivo validation measurements [FIG. 11].

In conclusion, the inventors have demonstrated the efficacy of a miniature LSI device to acquire perfusion data in the gingiva. There are many uses for a miniaturized LSI platform that is safe to use in the oral cavity. There are numerous clinical options for continuing to measure gingival blood flow, such as monitoring the effectiveness of new gingivitis treatments. Additionally, it may be possible to use regional LSI measurements to diagnose early stage gingivitis, before the appearance of clinical symptoms; for example, if one region exhibits significantly different SFI values than the rest of the mouth it may provide a clue for dentists to conduct preventative treatment. In addition to gingivitis, there are other conditions that affect the oral mucosa, for which the miniature LSI device may be used. For example, LSI may be used to provide a quantitative assessment of oral mucositis, an inflammatory condition causing painful ulcers in the mouth following chemotherapy and radiation treatments for cancer. Furthermore, the miniaturized mouth-guard based LSI device disclosed herein may provide a more stable method of collecting LSI data, and for more specifically targeting locations on the tooth that correspond to the pulpal chamber to reduce contamination of the signal from gingival blood flow.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a," "an," and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:

1. A method of detecting and quantifying gingivitis in a gingival region of an individual, the method comprising the steps of:
   quantitatively measuring blood flow within a portion of the gingival region at a plurality of time points by:
      capturing a sequence of speckle images of said portion of the gingival region using laser speckle imaging via a coherent light source and a detector, the light source configured for transmitting light through the gingival region, and the detector configured for detecting transmission of light from the light source through the gingival region;
      dividing each of the captured speckle images into a plurality of pixel points;
      for each of the pixel points, extracting an intensity value corresponding to the amount of transmitted light from the light source, said intensity value represented as a function of time relative to the time point at which the associated speckle image was captured by the detector;
      calculating a standard deviation of the extracted intensity values;
      calculating a mean intensity of the extracted intensity values;
      calculating a speckle contrast for said portion of the gingival region as the standard deviation of the extracted intensity values divided by the mean intensity; and
      calculating a speckle flow index value for said portion of the gingival region as a proportion of $1/K^2$, where K is the speckle contrast for said portion of the gingival region; and
   determining the presence of gingivitis in said portion of the gingival region wherein the speckle flow index value associated with said portion of the gingival region falls outside of a pre-determined range;
   whereby, the method is capable of determining the presence of gingivitis in the gingival region at a relatively early stage, prior to the appearance of clinical symptoms.

2. The method of claim 1, wherein the blood flow is measured in real time.

3. The method of claim 1, further comprising the step of treating the individual diagnosed with gingivitis by administering an effective amount of a medical composition for treating the gingivitis.

4. The method of claim 1, wherein the light source is directed onto said portion of the gingival region by one or more optics.

5. The method of claim 1, wherein the step of determining the presence of gingivitis in said portion of the gingival region further comprises the step of comparing the speckle flow index value associated with said portion of the gingival region to a pre-determined range based on the measured blood flow of a healthy subject.

6. The method of claim 1, further comprising the steps of:
   forming a custom-fit impression mold of a region of interest comprising at least a portion of the individual's upper teeth and gingival region;

forming an at least one pair of mold apertures in the mold, each of the at least one pair of mold apertures comprising a buccal aperture positioned on a buccal side of the mold and a corresponding lingual aperture positioned on an opposing lingual side of the mold, such that said buccal and lingual apertures are substantially linearly aligned with one another and a portion of the gingival region within the region of interest is substantially positioned therebetween; and for each of the at least one pair of mold apertures:
positioning the light source within a one of the buccal and lingual apertures of said pair of mold apertures;
positioning the detector within the other of the buccal and lingual apertures of said pair of mold apertures; and
positioning the mold within the individual's mouth so that a portion of the gingival region within the region of interest is substantially positioned between the buccal and lingual apertures of said pair of mold apertures.

7. The method of claim 6, further comprising the steps of:
forming a first pair of mold apertures located proximal an interdental papilla of the gingival region, between the individual's upper incisors, the first pair of mold apertures consisting of a buccal aperture in a buccal side of the mold and a corresponding lingual aperture in an opposing lingual side of the mold, such that said buccal and lingual apertures are substantially linearly aligned with one another and the interdental papilla of the gingival region is substantially positioned therebetween;
forming a second pair of mold apertures located proximal a marginal gingiva of the gingival region, the second pair of mold apertures consisting of a buccal aperture in the buccal side of the mold and a corresponding lingual aperture in the lingual side of the mold, such that said buccal and lingual apertures are substantially linearly aligned with one another and the marginal gingiva of the gingival region is substantially positioned therebetween;
forming a third pair of mold apertures located proximal an attached gingiva of the gingival region, the third pair of mold apertures consisting of a buccal aperture in the buccal side of the mold and a corresponding lingual aperture in the lingual side of the mold, such that said buccal and lingual apertures are substantially linearly aligned with one another and the attached gingiva of the gingival region is substantially positioned therebetween; and
forming a fourth pair of mold apertures located proximal an alveolar mucosa of the gingival region, the fourth pair of mold apertures consisting of a buccal aperture in the buccal side of the mold and a corresponding lingual aperture in the lingual side of the mold, such that said buccal and lingual apertures are substantially linearly aligned with one another and the alveolar mucosa of the gingival region is substantially positioned therebetween.

8. The method of claim 6, wherein the step of forming a custom-fit impression mold further comprises the step of forming the custom-fit impression mold using dental putty.

9. The method of claim 6, wherein the step of forming an at least one pair of mold apertures in the mold further comprises the step of forming the at least one pair of mold apertures in the mold using a drill.

10. The method of claim 1, wherein the step of calculating a speckle flow index value for said portion of the gingival region further comprises the step of calculating the speckle flow index value as $1/(2TK^2)$, where T is an exposure time of the detector and K is the speckle contrast for said portion of the gingival region.

11. The method of claim 10, wherein the step of quantitatively measuring blood flow within said portion of the gingival region at a plurality of time points further comprises the step of setting the exposure time of the detector to between approximately 2-23 milliseconds.

12. The method of claim 11, wherein the step of setting the exposure time of the detector comprises the step of setting the exposure time of the detector to approximately 10 milliseconds.

13. The method of claim 1, wherein the detector is a miniature camera.

14. The method of claim 1, wherein the light source is a near-infrared laser diode.

15. A method of detecting and quantifying gingivitis in a gingival region of an individual, the method comprising the steps of:
forming a custom-fit impression mold of a region of interest comprising at least a portion of the individual's upper teeth and gingival region;
forming an at least one pair of mold apertures in the mold, each of the at least one pair of mold apertures comprising a buccal aperture positioned on a buccal side of the mold and a corresponding lingual aperture positioned on an opposing lingual side of the mold, such that said buccal and lingual apertures are substantially linearly aligned with one another and a portion of the gingival region within the region of interest is substantially positioned therebetween; and
for each of the at least one pair of mold apertures:
positioning a coherent light source within a one of the buccal and lingual apertures of said pair of mold apertures, the light source configured for transmitting light through the gingival region;
positioning a detector within the other of the buccal and lingual apertures of said pair of mold apertures, the detector configured for detecting transmission of light from the light source through the gingival region;
positioning the mold within the individual's mouth so that a portion of the gingival region within the region of interest is substantially positioned between the buccal and lingual apertures of said pair of mold apertures;
quantitatively measuring blood flow within said portion of the gingival region at a plurality of time points by:
capturing a sequence of speckle images of said portion of the gingival region using laser speckle imaging via the light source and detector;
dividing each of the captured speckle images into a plurality of pixel points;
for each of the pixel points, extracting an intensity value corresponding to the amount of transmitted light from the light source, said intensity value represented as a function of time relative to the time point at which the associated speckle image was captured by the detector;
calculating a standard deviation of the extracted intensity values;
calculating a mean intensity of the extracted intensity values;

calculating a speckle contrast for said portion of the gingival region as the standard deviation of the extracted intensity values divided by the mean intensity; and calculating a speckle flow index value for said portion of the gingival region as a proportion of $1/K^2$, where K is the speckle contrast for said portion of the gingival region; and determining the presence of gingivitis in said portion of the gingival region wherein the speckle flow index value associated with said portion of the gingival region falls outside of a pre-determined range;

whereby, the method is capable of determining the presence of gingivitis in the gingival region at a relatively early stage, prior to the appearance of clinical symptoms.

16. A method of detecting and quantifying gingivitis in a gingival region of an individual, the method comprising the steps of:

forming a custom-fit impression mold of a region of interest comprising at least a portion of the individual's upper teeth and gingival region;

forming an at least one pair of mold apertures in the mold, each of the at least one pair of mold apertures comprising a buccal aperture positioned on a buccal side of the mold and a corresponding lingual aperture positioned on an opposing lingual side of the mold, such that said buccal and lingual apertures are substantially linearly aligned with one another and a portion of the gingival region within the region of interest is substantially positioned therebetween; and for each of the at least one pair of mold apertures:

positioning a coherent light source within a one of the buccal and lingual apertures of said pair of mold apertures, the light source configured for transmitting light through the gingival region;

positioning a detector within the other of the buccal and lingual apertures of said pair of mold apertures, the detector configured for detecting transmission of light from the light source through the gingival region;

positioning the mold within the individual's mouth so that a portion of the gingival region within the region of interest is substantially positioned between the buccal and lingual apertures of said pair of mold apertures;

quantitatively measuring blood flow within said portion of the gingival region at a plurality of time points by:

capturing a sequence of speckle images of said portion of the gingival region using laser speckle imaging via the light source and detector;

dividing each of the captured speckle images into a plurality of pixel points;

for each of the pixel points, extracting an intensity value corresponding to the amount of transmitted light from the light source, said intensity value represented as a function of time relative to the time point at which the associated speckle image was captured by the detector;

calculating a standard deviation of the extracted intensity values;

calculating a mean intensity of the extracted intensity values;

calculating a speckle contrast for said portion of the gingival region as the standard deviation of the extracted intensity values divided by the mean intensity; and calculating a speckle flow index value for said portion of the gingival region as $1/(2TK^2)$, where T is an exposure time of the detector and K is the speckle contrast for said portion of the gingival region; and determining the presence of gingivitis in said portion of the gingival region wherein the speckle flow index value associated with said portion of the gingival region falls outside of a pre-determined range;

whereby, the method is capable of determining the presence of gingivitis in the gingival region at a relatively early stage, prior to the appearance of clinical symptoms.

\* \* \* \* \*